US007459302B2

(12) United States Patent
Reid et al.

(10) Patent No.: US 7,459,302 B2
(45) Date of Patent: Dec. 2, 2008

(54) SIDE-WALL HEATER FOR THERMOCYCLER DEVICE

(75) Inventors: Taylor Reid, Carlsbad, CA (US); Roger Taylor, San Diego, CA (US); Larry Brown, Carlsbad, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 10/261,751

(22) Filed: Oct. 1, 2002

(65) Prior Publication Data

US 2003/0106682 A1 Jun. 12, 2003

Related U.S. Application Data

(60) Provisional application No. 60/346,114, filed on Oct. 19, 2001, provisional application No. 60/326,599, filed on Oct. 2, 2001.

(51) Int. Cl.
*C12M 1/38* (2006.01)

(52) U.S. Cl. ................. 435/286.1; 435/303.1; 435/809; 435/91.2; 435/288.7; 422/99; 422/104; 165/206

(58) Field of Classification Search ..................... 435/6, 435/91.2, 286.1, 287.2, 288.3, 288.4, 288.7, 435/303.1, 305.1-305.4, 809; 219/385, 386, 219/428; 422/99, 104, 102

See application file for complete search history.

(56) References Cited

U.S. PATENT DOCUMENTS 5,645,801 A * 7/1997 Bouma et al. .............. 422/68.1
5,670,120 A 9/1997 Degenhardt et al. .......... 422/104
6,153,426 A * 11/2000 Heimberg ................ 435/287.2
6,638,761 B2 * 10/2003 Shin et al. ................ 435/288.4

FOREIGN PATENT DOCUMENTS

| | | | |
|---|---|---|---|
| DE | 3441179 | A1 | 5/1986 |
| DE | 42 17 868 | A1 | 12/1993 |
| EP | 0 488 769 | A2 | 6/1992 |
| WO | WO 89/10789 | | 11/1989 |

OTHER PUBLICATIONS

International Search Report of International Application No. PCT/US02/31143, Feb. 14, 2003.

* cited by examiner

*Primary Examiner*—William H. Beisner

(57) ABSTRACT

The invention relates to an apparatus and methods for preventing condensation on the interior surfaces of sample tubes which are being exposed to temperature cycles, such as during a PCR amplification reaction. In particular, the invention relates to apparatus comprising a sample block comprising a plurality of sample wells for receiving sample tubes and heating elements disposed in the sample wells for heating at least a portion of the sides of sample tubes (e.g., at least the portion which forms the head space after a tube is filled with a PCR reaction mixture). In a preferred aspect, the sample block is part of a thermocycling device for performing PCR and the side-wall heater is used to enhance uniformity and speed of amplification reactions. For example, by decreasing or eliminating condensation, signal strength jumps in a real-time PCR assay can be minimized as can reaction non-homogeneity.

40 Claims, 9 Drawing Sheets

Tubes showing no side wall condensation after thermocycling with the use of the side wall heater

| R Last | dR Last | Rn Last | dRn Last | RLast/RFirst | Threshhold | Well | Ct | | a | b | c | d | e | f | g | h |
|---|---|---|---|---|---|---|---|---|---|---|---|---|---|---|---|---|
| 3407 | 1666.19 | 0.234 | 0.115 | 2.258 | 0.0004 | A1 | 17.99 | 1 | 17.99 | 18.3 | 18.11 | 18.24 | 18.29 | 18.23 | 18.03 | 18.09 |
| 3492 | 1787.762 | 0.205 | 0.102 | 2.243 | 0.0004 | A2 | 18.13 | 2 | 18.13 | 18.16 | 18.13 | 18.28 | 18.05 | 18.21 | 18.09 | 18.29 |
| 3369 | 1701.881 | 0.206 | 0.1 | 2.211 | 0.0004 | A3 | 18.2 | 3 | 18.2 | 18.29 | 18.28 | 18.34 | 18.35 | 18.31 | 18.11 | 18.17 |
| 3634 | 1839.5 | 0.211 | 0.104 | 2.188 | 0.0004 | A4 | 18.18 | 4 | 18.18 | 18.03 | 18.07 | 18.31 | 18.15 | 18.12 | 18.17 | 18 |
| 3784 | 1942.024 | 0.214 | 0.108 | 2.184 | 0.0004 | A5 | 18.22 | 5 | 18.22 | 18.36 | 18.25 | 18.25 | 18.12 | 18.34 | 18.09 | 18.05 |
| 3485 | 1798.071 | 0.213 | 0.108 | 2.203 | 0.0004 | A6 | 18.11 | 6 | 18.11 | 18.1 | 18.44 | 18.26 | 18.24 | 18.17 | 18.25 | 18.5 |
| 3376 | 1718.857 | 0.217 | 0.106 | 2.293 | 0.0004 | A7 | 18.35 | 7 | 18.35 | 18.47 | 18.28 | 18.33 | 18.4 | 18.22 | 18.15 | 17.89 |
| 3085 | 1572.19 | 0.208 | 0.107 | | | | | | | | | | 18.34 | 18.11 | 18.16 | 18.15 |
| 3244 | 1561 | 0.209 | 0.101 | | | | | | | | | | 18.1 | 18.28 | 18.1 | 18.17 |
| 3129 | 1598.714 | 0.212 | 0.105 | | | | | | | | | | 18.16 | 18.13 | 18.13 | 18.13 |
| 2972 | 1461.571 | 0.204 | 0.098 | | | | | | | | | | 18.03 | 17.85 | 18.01 | 17.89 |
| 3253 | 1694.238 | 0.225 | 0.114 | | | | | | | | | | 18.43 | 18.47 | 18.32 | 18.22 |
| 3578 | 1813.524 | 0.207 | 0.104 | | | | | | | | | | | | | |
| 3591 | 1835.5 | 0.211 | 0.107 | | | | | | | | | | | | | |
| 3492 | 1765.595 | 0.206 | 0.102 | | | | | | | | | | | | | |
| 3556 | 1787.667 | 0.205 | 0.103 | | | | | | | | | | | | | |
| 3646 | 1845.667 | 0.212 | 0.103 | | | | | | | | | | | | | |
| 3551 | 1844.929 | 0.209 | 0.106 | | | | | | | | | | | | | |
| 3226 | 1570.667 | 0.199 | 0.095 | | | | | | | | | | | | | |
| 3437 | 1784.381 | 0.215 | 0.11 | | | | | | | | | | | | | |
| 3497 | 1783.119 | 0.213 | 0.103 | | | | | | | | | | | | | |
| 3445 | 1685.119 | 0.219 | 0.103 | | | | | | | | | | | | | |
| 3314 | 1653.452 | 0.208 | 0.102 | | | | | | | | | | | | | |
| 3298 | 1684.19 | 0.217 | 0.108 | | | | | | | | | | | | | |
| 3637 | 1860.071 | 0.21 | 0.107 | | | | | | | | | | | | | |
| 3851 | 1973.571 | 0.206 | 0.105 | | | | | | | | | | | | | |
| 3547 | 1840.31 | 0.207 | 0.106 | | | | | | | | | | | | | |
| 3388 | 1735.929 | 0.223 | 0.111 | | | | | | | | | | | | | |
| 3431 | 1728.357 | 0.213 | 0.106 | | | | | | | | | | | | | |
| 3357 | 1614.071 | 0.201 | 0.094 | | | | | | | | | | | | | |
| 3467 | 1699.31 | 0.196 | 0.095 | | | | | | | | | | | | | |
| 3638 | 1911.69 | 0.215 | 0.111 | | | | | | | | | | | | | |
| 3355 | 1702.738 | 0.208 | 0.104 | | | | | | | | | | | | | |
| 3539 | 1765.857 | 0.211 | 0.102 | | | | | | | | | | | | | |
| 3623 | 1768.357 | 0.206 | 0.099 | | | | | | | | | | | | | |
| 3408 | 1721.238 | 0.219 | 0.109 | | | | | | | | | | | | | |
| 3575 | 1824.667 | 0.213 | 0.107 | | | | | | | | | | | | | |
| 3914 | 1996.976 | 0.208 | 0.106 | | | | | | | | | | | | | |
| 3566 | 1808.357 | 0.21 | 0.105 | | | | | | | | | | | | | |
| 3659 | 1868.119 | 0.206 | 0.104 | | | | | | | | | | | | | |
| 3763 | 1912.81 | 0.207 | 0.105 | | | | | | | | | | | | | |
| 3469 | 1709.333 | 0.196 | 0.097 | | | | | | | | | | | | | |
| 3559 | 1739.167 | 0.2 | 0.096 | 2.611 | 0.0004 | D7 | 18.33 | | | | | | | | | |
| 3658 | 1854.476 | 0.209 | 0.105 | 2.517 | 0.0004 | D8 | 18.3 | | | | | | | | | |
| 3630 | 1877.452 | 0.203 | 0.102 | 2.134 | 0.0004 | D9 | 18.2 | | | | | | | | | |
| 3525 | 1752.738 | 0.209 | 0.102 | 2.072 | 0.0004 | D10 | 18.15 | | | | | | | | | |
| 3666 | 1848.214 | 0.214 | 0.108 | 2.114 | 0.0004 | D11 | 17.81 | | | | | | | | | |
| 3545 | 1757.833 | 0.21 | 0.103 | 2.153 | 0.0004 | D12 | 18.28 | | | | | | | | | |
| 3406 | 1677.595 | 0.204 | 0.099 | 2.188 | 0.0004 | E1 | 18.29 | | | | | | | | | |
| 3678 | 1916.929 | 0.206 | 0.107 | 2.173 | 0.0004 | E2 | 18.05 | | | | | | | | | |
| 3632 | 1855.952 | 0.204 | 0.103 | 2.168 | 0.0004 | E3 | 18.35 | | | | | | | | | |

FIGURE 4

FIGURE 4 cont.

| R Last | dR Last | Rn Last | dRn Last | RLast/RFirst | Threshhold | Well | Ct |
|---|---|---|---|---|---|---|---|
| 3539 | 1847.524 | 0.207 | 0.106 | 2.201 | 0.0004 | E4 | 18.15 |
| 3943 | 2037.143 | 0.211 | 0.107 | 2.438 | 0.0004 | E5 | 18.12 |
| 3400 | 1619.214 | 0.197 | 0.093 | 2.569 | 0.0004 | E6 | 18.24 |
| 3664 | 1778.5 | 0.199 | 0.095 | 2.689 | 0.0004 | E7 | 18.4 |
| 3774 | 1896.214 | 0.215 | 0.0106 | 2.725 | 0.0004 | E8 | 18.34 |
| 3649 | 1869.238 | 0.2 | 0.102 | 2.159 | 0.0004 | E9 | 18.1 |
| 3695 | 1839.69 | 0.211 | 0.101 | 2.055 | 0.0004 | E10 | 18.16 |
| 3784 | 1856.786 | 0.206 | 0.1 | 2.145 | 0.0004 | E11 | 18.03 |
| 3432 | 1685.571 | 0.215 | 0.104 | 2.091 | 0.0004 | E12 | 18.43 |
| 3591 | 1758.048 | 0.199 | 0.097 | 2.129 | 0.0004 | F1 | 18.23 |
| 3924 | 1950.619 | 0.226 | 0.111 | 2.084 | 0.0004 | F2 | 18.21 |
| 3458 | 1725.357 | 0.208 | 0.103 | 2.188 | 0.0004 | F3 | 18.31 |
| 3686 | 1931.881 | 0.205 | 0.107 | 2.205 | 0.0004 | F4 | 18.12 |
| 3655 | 1759.071 | 0.206 | 0.098 | 2.197 | 0.0004 | F5 | 18.34 |
| 3759 | 1901.405 | 0.203 | 0.103 | 2.564 | 0.0004 | F6 | 18.17 |
| 3687 | 1895.214 | 0.207 | 0.105 | 2.58 | 0.0004 | F7 | 18.22 |
| 3939 | 2026.476 | 0.214 | 0.11 | 2.645 | 0.0004 | F8 | 18.11 |
| 3673 | 1850.571 | 0.202 | 0.101 | 2.184 | 0.0004 | F9 | 18.28 |
| 3705 | 1841.595 | 0.199 | 0.098 | 2.124 | 0.0004 | F10 | 18.13 |
| 3693 | 1794.238 | 209 | 0.101 | 2.119 | 0.0004 | F11 | 17.85 |
| 3635 | 1750.167 | 0.206 | 0.099 | 2.123 | 0.0004 | F12 | 18.47 |
| 3652 | 1878.048 | 0.219 | 0.113 | 2.216 | 0.0004 | G1 | 18.03 |
| 3723 | 1941.357 | 0.206 | 0.107 | 2.184 | 0.0004 | G2 | 18.09 |
| 3603 | 1856.548 | 0.211 | 0.107 | 2.148 | 0.0004 | G3 | 18.11 |
| 3602 | 1858.119 | 0.212 | 0.109 | 2.157 | 0.0004 | G4 | 18.17 |
| 3746 | 1920.738 | 0.208 | 0.106 | 2.165 | 0.0004 | G5 | 18.09 |
| 3402 | 1650.024 | 0.201 | 0.096 | 2.123 | 0.0004 | G6 | 18.25 |
| 3466 | 1699.476 | 0.208 | 0.102 | 2.146 | 0.0004 | G7 | 18.15 |
| 3785 | 1916.452 | 0.221 | 0.112 | 2.271 | 0.0004 | G8 | 18.16 |
| 3659 | 1822.452 | 0.202 | 0.101 | 2.052 | 0.0004 | G9 | 18.1 |
| 3701 | 1815.381 | 0.208 | 0.1 | 2.101 | 0.0004 | G10 | 18.13 |
| 3720 | 1844.048 | 0.213 | 0.105 | 2.1 | 0.0004 | G11 | 18.01 |
| 3693 | 1863.976 | 0.217 | 0.109 | 2.176 | 0.0004 | G12 | 18.32 |
| 3335 | 1690.905 | 0.212 | 0.106 | 2.3 | 0.0004 | H1 | 18.09 |
| 3257 | 1667.252 | 0.206 | 0.103 | 2.252 | 0.0004 | H2 | 18.29 |
| 3467 | 1706.69 | 0.212 | 0.103 | 2.16 | 0.0004 | H3 | 18.17 |
| 3527 | 1844.738 | 0.215 | 0.111 | 2.184 | 0.0004 | H4 | 18 |
| 3609 | 1831.667 | 0.224 | 0.112 | 2.275 | 0.0004 | H5 | 18.06 |
| 3230 | 1547.452 | 0.209 | 0.104 | 2.302 | 0.0004 | H6 | 18.5 |
| 3456 | 1744.762 | 0.215 | 0.109 | 2.264 | 0.0004 | H7 | 17.89 |
| 3606 | 1857.119 | 0.215 | 0.111 | 2.244 | 0.0004 | H8 | 18.15 |
| 3547 | 1717.714 | 0.203 | 0.096 | 2.117 | 0.0004 | H9 | 18.17 |
| 3519 | 1577.762 | 0.202 | 0.09 | 1.973 | 0.0004 | H10 | 18.13 |
| 3407 | 1650.024 | 0.205 | 0.099 | 2.192 | 0.0004 | H11 | 17.89 |
| 3500 | 1729.738 | 0.233 | 0.114 | 2.287 | 0.0004 | H12 | 18.22 |

SIDE-WALL HEATER FOR THERMOCYCLER DEVICE

RELATED APPLICATIONS

The present application claims the benefit of U.S. provisional application with Serial No. 60/326,599, filed Oct. 2, 2001 and U.S. provisional application with Serial No. 60/346,114, filed Oct. 19, 2001, the entirety of each is incorporated herein by reference.

FIELD OF THE INVENTION

The invention relates to a side-wall heater for use in a thermocycler device.

BACKGROUND OF THE INVENTION

Polymerase chain reaction (PCR) exponentially amplifies DNA using temperature cycling to generate millions of copies of a target nucleic acid sequence from limited starting amounts of nucleic acids. Generally during PCR, target DNA is amplified by denaturing the DNA, annealing short primers to resulting single strands at specific sites (e.g., sequences flanking the target site) and extending the primers using a thermostable polymerase to generate new copies of double-stranded DNA complementary to the target. Typically, the PCR reaction mixture is repeatedly cycled (e.g., 20-50 times) from high temperatures (e.g., >90° C.) to denature the DNA to lower temperatures (e.g., between about 37° C. to 70° C.) for primer annealing and extension. Primer annealing and extension can be performed at the same or different temperatures.

In most automated PCR instruments, the reaction mixture is placed within a disposable plastic tube which is closed with a cap and placed within a metal heat-conducting sample block. The sample block is in communication with a processor which controls the cyclical heating of the block. As the metal block changes temperature, the reaction mixture is exposed to similar changes in temperature. Generally, PCR instruments provide a heating element at the bottom of the sample block in the form of a Peltier thermoelectric device or a thin foil heating element (MINCO brand, Minneapolis, Minn.) or alternatively supply a heated or cooled fluid through channels machined into the sample block. The use of these types of heating devices can result in delays in transferring heat from the sample block to the reaction mixture which may not be the same for all samples. Thus, both the efficiency and uniformity of amplification of nucleic acids within the samples can suffer as a consequence.

Evaporation from the PCR mixture during thermal cycling also can decrease the uniformity of amplification. Since the reaction mixture generally occupies only a fraction of a sample tube, this leaves a volume of air (known as "head space") above the reaction mixture into which the reagents of the reaction can evaporate and subsequently condense. Various strategies have been used to minimize this problem. For example, a hydrophobic material such as mineral oil can be layered onto the PCR reaction mixture. The hydrophobic material floats on the reaction mixture and completely covers the surface of the reaction mixture, preventing evaporation from the mixture and condensation onto the side walls of the sample tube. A variant method relies on the use of a small solid wax ball or grease that melts at denaturing temperatures and which can be used to cover the surface of the reaction mixture (see, e.g., as described in U.S. Pat. No. 5,411,876). A commercially available wax ball used for this purpose is AMPLIWAX available from PERKIN-ELMER, Norwalk, Conn., U.S.A. However, adding hydrophobic materials or wax balls to the reaction mixture is both time consuming and increases the probability of sample contamination.

Another strategy to prevent or minimize sample evaporation and condensation includes the use of an external heater which is in proximity with the sample block. For example, the Stratagene Hot Top Assembly™ hot top for the RoboCycler® thermocycler provides a mechanism for heating the top of sample tubes placed in a sample block while the thermocycler's heating element heats the bottom of the sample block. The Hot Top Assembly™ significantly reduces condensation but a slight ring of condensation above the PCR reaction mixture in sample tubes may still be observed.

SUMMARY OF THE INVENTION

The invention relates to an apparatus and methods for preventing condensation on the interior surfaces of sample tubes which are exposed to temperature cycles, such as during a PCR amplification reaction. In particular, the invention relates to apparatus comprising a sample block comprising a plurality of sample wells for receiving sample tubes and heating elements for heating at least a portion of the sides of sample tubes (e.g., at least the portion which forms the head space after a tube is filled with a PCR reaction mixture). In a preferred aspect, the sample block is part of a thermocycling device for performing PCR and the side-wall heater is used to enhance uniformity and speed of amplification reactions. For example, by decreasing or eliminating condensation, signal strength jumps in a real-time PCR assay can be minimized as can reaction non-homogeneity.

In one aspect, the invention provides an apparatus for heating an upper portion of the interior surface of a sample tube, the upper portion extending from the top of the tube to a point above a lower portion of the tube which is filled with a fluid. The apparatus comprises a side-wall heating block which comprises a heat-conducting material (e.g., such as aluminum) and at least one sample hole for receiving the sample tube. The sample hole runs from an upper surface of the block through a lower surface of said block and is alignable with a sample well of a sample block for a thermocycler apparatus. The heating block further comprises a heating element (e.g., such as a resistive heating element) disposed on or in the side-wall heating block. The heating element is connectable (directly or indirectly) to a power supply for activating the heating element to thereby provide heat to the heat-conducting material.

In a preferred aspect, the heating block further comprises a temperature sensor for detecting the temperature of the block. The temperature sensor is connectable to a processor for monitoring the temperature of the block, the processor being connectable to the power supply and for providing instructions to the power supply to activate the heating element to maintain the temperature of the block to a level which is the same or higher than the temperature of a fluid in the lower portion of the tube for a selected period of time.

Preferably, the side-wall heating block comprises a plurality of sample holes for receiving a plurality of sample tubes. In one aspect, at least one sample hole is conformed to fit a sample tube for use in a PCR reaction such that the sample tube does not freely rotate in said sample hole or there is 1 mm or less of space between the walls of the sample hole and the external walls of the sample tube.

In one aspect, the sample tube can receive up to 0.2 ml of a fluid. In another aspect, the sample tube can receive up to 0.6 ml of a fluid. In still another aspect, the sample tube can receive up to 1.5 ml of a fluid. In a further aspect, the sample tube is connected to a plurality of other sample tubes, each other sample tube received by a sample hole in the side-wall heating block, i.e., the sample tubes are connected as a strip of sample tubes. In this scenario, the "top" of each tube extends from the portion of the tube which rests at the top of the sample hole.

The side-wall heating block can comprise any number of sample holes. In one aspect, the block comprises 24 sample holes, 32 sample holes, 48 sample holes, 96 sample holes, or 384 sample holes. Preferably, the sample holes are arrayed as in a standard microtiter plate format. In one aspect, the sample holes are arrayed in 8 rows. In another aspect, the sample holes are arrayed in three, four, six, or twelve columns.

The invention further provides an assembly comprising an apparatus as described above and a sample block for a thermocycler comprising at least one sample well, wherein any sample holes in the side-wall heating block are aligned with openings of any sample wells in the sample block. In one aspect, the sample block comprises a heating element and the heating element in the side-wall heating block is controllable independently of said heating element in the sample block. Preferably, the sample block further comprises a cooling element. In one aspect, the at least one sample well in the sample block is beveled to receive a conical portion of a sample tube comprising a conical portion and a cylindrical portion. The sample hole of the side-wall heating block is conformed to receive the cyclindrical portion of the sample tube.

The invention also provides a thermocycler device comprising the assembly described above. In one aspect, the thermocycler device further comprises a hot top assembly for heating the external surface of the top of the at least one sample tube placed in a sample hole in the side-wall heating block.

In a further aspect, the thermocycler device is connectable to a detector for detecting optical signals from an at least one sample tube disposed in the assembly. Preferably, the detector enables detection of a signal generated during the progress of an amplification reaction.

The invention also provides a method for heating the upper portion of a sample tube above a portion of the tube which is filled with a fluid (e.g., such as a reaction mixture used in an amplification reaction). The method comprises placing the sample tube in a sample hole of the apparatus as described above, the portion of the tube comprising the fluid protruding past the lower surface of the side-wall heating block and activating the heating element to heat the upper portion of the sample tube. Preferably, the side-wall heating block is heated to a temperature which is the same or above the temperature of the portion of the tube comprising the fluid. Heating of the side-wall heating block can be used to prevent condensation on interior walls of said sample tube.

In one aspect, the portion of the tube comprising the fluid is within a sample well of a sample block which comprises a heating element which is controlled independently of the heating element in the side-wall heating block. Preferably, the sample block cycles the portion of the tube comprising the fluid through a least one change of temperature. More preferably, the sample block cycles the portion of the tube comprising the fluid through cycles of a PCR reaction.

In one aspect, the heating element in the side-wall heating block maintains the side-wall heating block at a temperature which is the same or above the temperature of the sample block for a selected period of time (e.g., throughout the course of a PCR reaction, such as for at 20-50 cycles of a PCR reaction). In a preferred aspect, the heating element of the side-wall heating block maintains the side-wall heating block at a temperature which is above the highest temperature through which the sample block is cycling (e.g., at a temperature greater than 90° C., and preferably greater than 94° C., where the cycling is part of a PCR reaction). In a preferred aspect, the side-wall heating block maintains a uniform temperature while the sample block is cycling through changes of temperature.

BRIEF DESCRIPTION OF THE FIGURES

The objects and features of the invention can be better understood with reference to the following detailed description and accompanying drawings. The drawings are not to scale.

FIG. 1 shows a diagram of an assembly configured for one tube; the positions of the tube within the heating block and sample block are shown by means of dotted lines.

FIG. 4 is a table showing a demonstrating uniformity of PCR amplification obtained using the side-wall heating apparatus according to one aspect of the invention.

DETAILED DESCRIPTION

The invention provides an apparatus for heating at least a portion of the upper walls of sample tubes placed within the sample wells of a sample block adapted to receive the lower portion of the sample tubes. Preferably, the apparatus is conformed in size and shape to fit within a thermocycler apparatus adapted to hold one or more sample blocks (e.g., such as Stratagene®'s Mx 4000 or RoboCycler® thermocycler).

Definitions

The following definitions are provided for specific terms which are used in the following written description.

As used herein, the term "block" refers to a structure, usually metal, which can be temperature controlled and in which wells or holes have been arranged to accept tubes containing reaction mixtures or "samples."

As used herein, "head space" refers to empty space within a sample tube which has been partially filled with a fluid (e.g., such a reaction mixture). In one aspect, head space is at least $\frac{2}{3}$, $\frac{1}{2}$, $\frac{1}{3}$, $\frac{3}{4}$, $\frac{9}{10}$, $\frac{4}{5}$, or $\frac{14}{15}$ of the total volume of a sample tube. In another aspect, head space is the space remaining after a 0.2 ml, a 0.5 ml, a 1 ml, or a 1.5 ml tube is filled with 10, 20, 50, 100, or 200 μl of a fluid, such as a reaction mixture.

As used herein, a "reaction mixture" refers to a volume of fluid comprising one or more of a buffer for a PCR reaction, one or more nucleotides, a polymerase, and a sample containing or suspected of containing a nucleic acid.

As used herein, the "upper section of a sample tube" or the "upper portion of a sample tube" refers to a portion of a sample tube from the top of the tube to approximately the midpoint of the sample tube or to a point between the midpoint and the top of the tube. In one aspect, the upper section is 1 mm, 2 mm, 3 mm, 4 mm, 5 mm in length.

Figure 2:
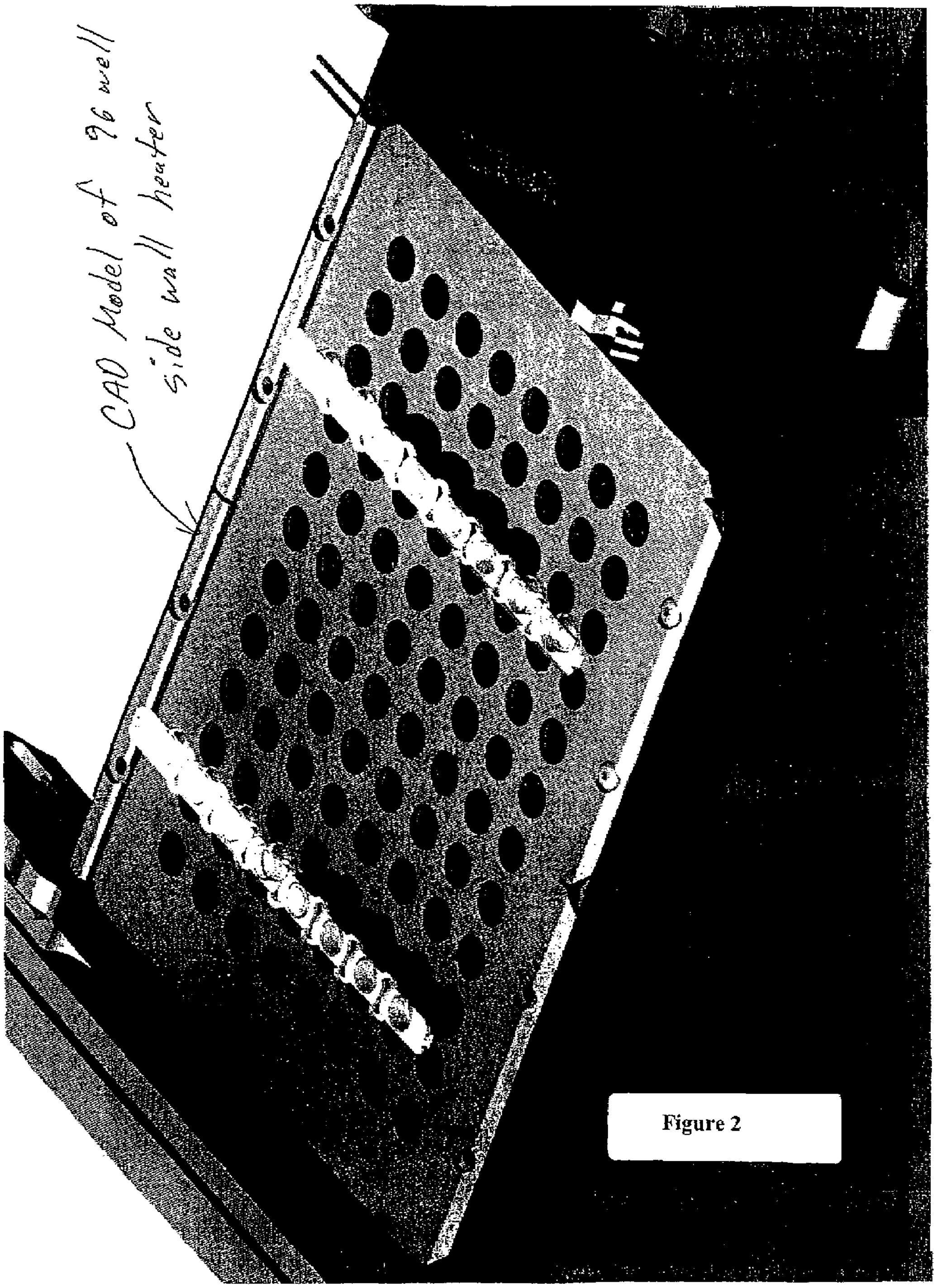
FIG. 2 shows a photograph of an assembly configured for multiple tubes according to one aspect of the invention.
Figure 3:
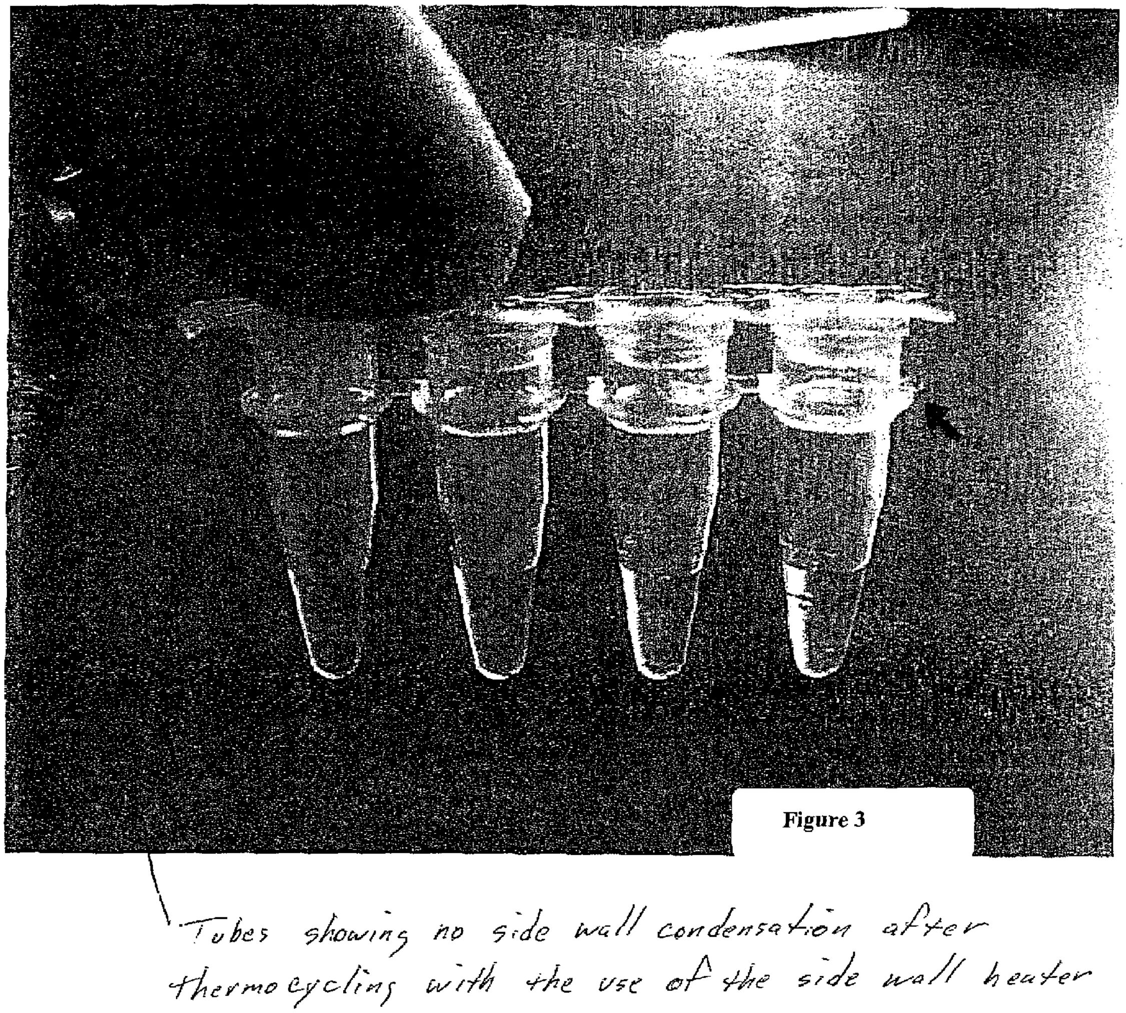
FIG. 3 shows sample tubes showing no side wall condensation after thermocycling with the use of the side-wall heating block.
Figure 5:
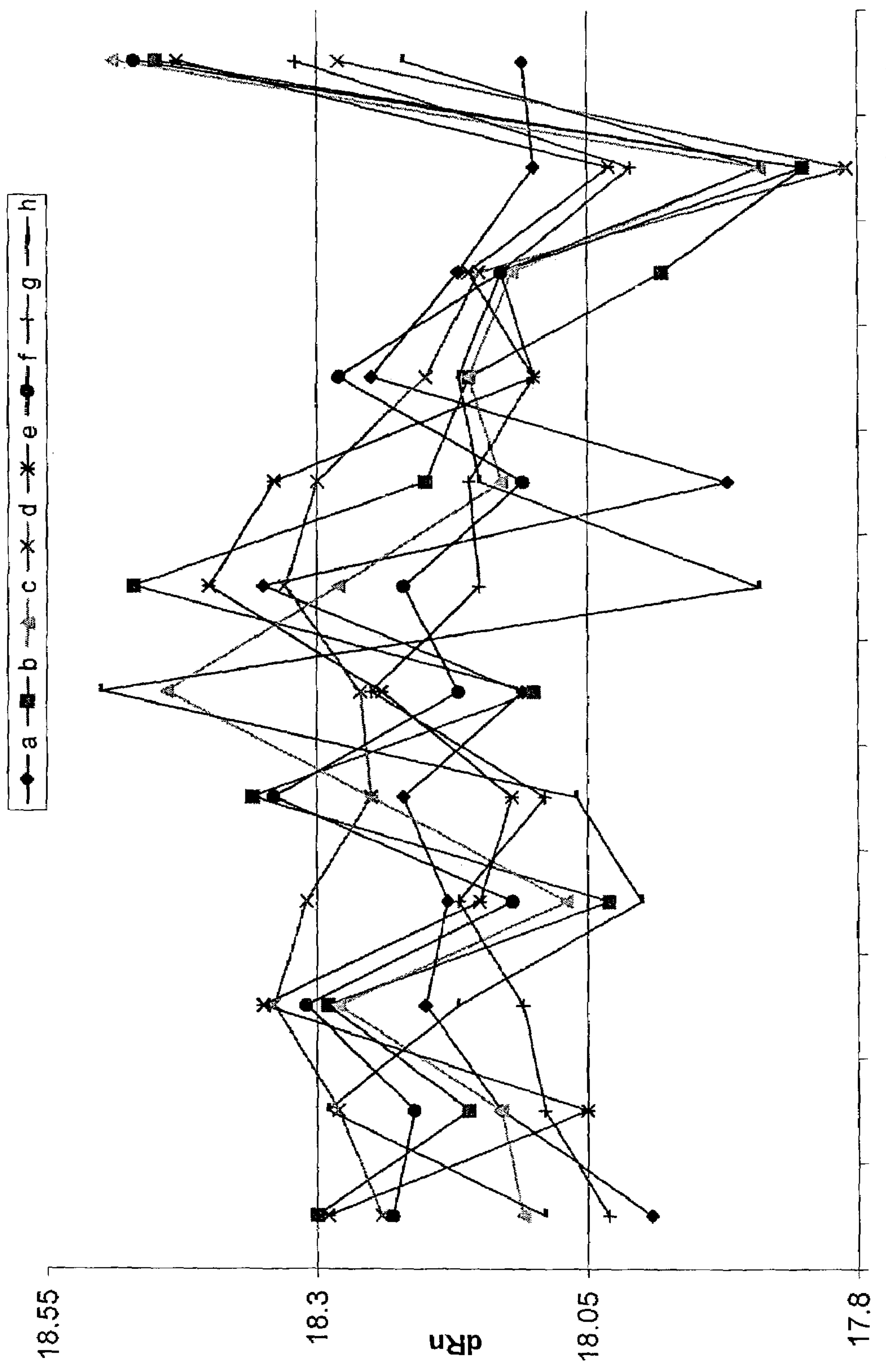
FIG. 5 is a plot showing the uniformity of PCR amplification in different sample tubes placed in the side-wall heating apparatus according to one aspect of the invention.
Figure 6:
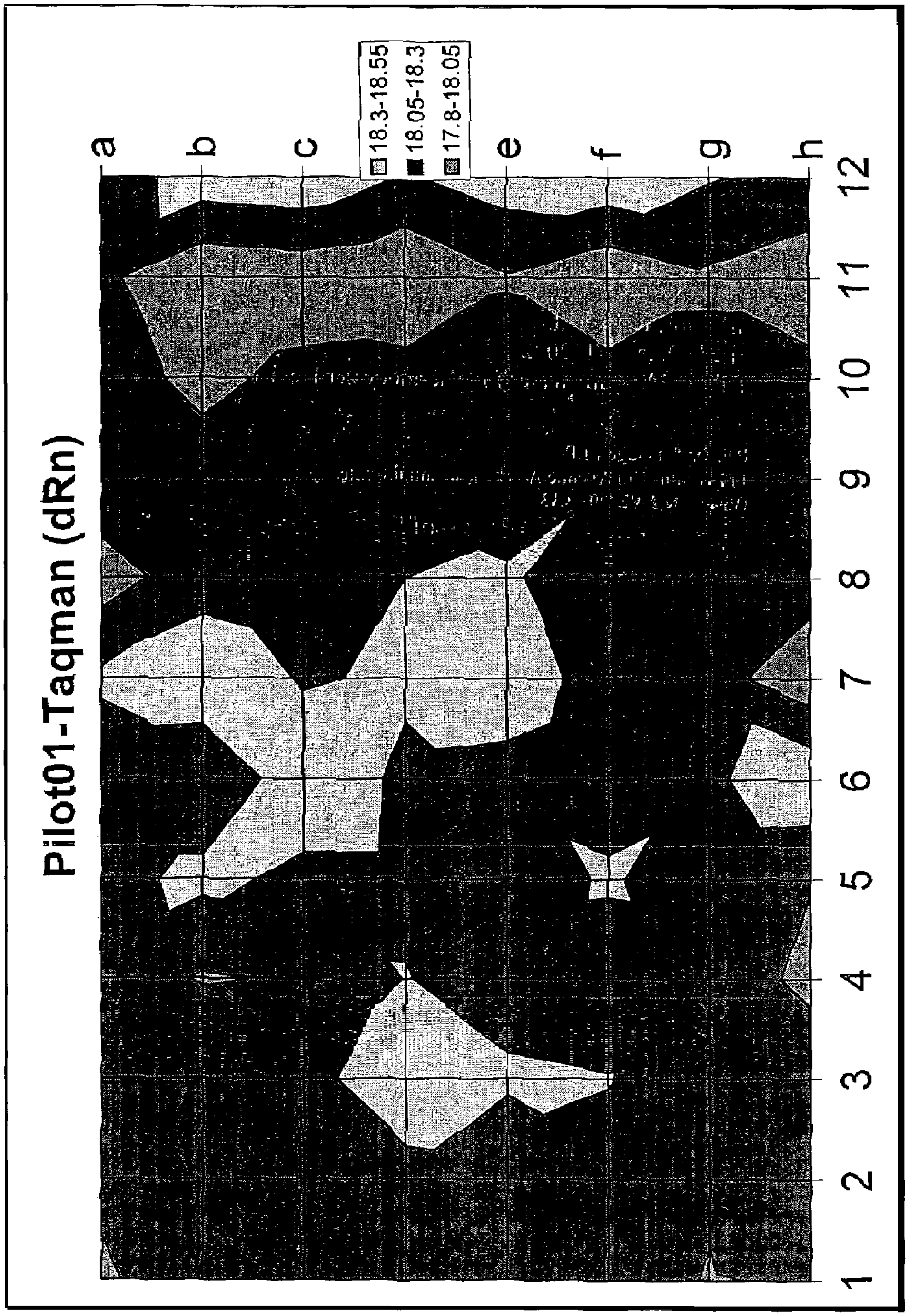
FIG. 6 is a contour plot schematically illustrating the amplification uniformity shown in FIG. 2B according to one aspect of the invention.

As used herein, the "top of the tube" refers to the section of the tube which extends from the part of the tube which rests at the top of the side-wall heating block. In one aspect, the "top of the tube" extends from the lid of the tube or from the portion of the tube which is capped when a tube is capped. However, in another aspect, where the tube is part of a strip of tubes (see, e.g., as shown in FIG. 3), the top of the tube extends from the strip which connects the tubes as the strip will rest at the top of the side-wall heating block (see, e.g., as shown in FIG. 2).

As used herein, the "lower portion of the tube" refers to at least the portion of the tube which comprises a fluid such as a reaction mixture.

As used herein, a "side-wall heater" refers to a heating element for heating at least an upper portion of the side-walls of a sample tube or the head space of a sample tube, such as a PCR or eppendorf tube.

As defined herein, "decreasing or preventing or eliminating condensation" refers to a lack of visible condensation of the side-walls of a sample tube immediately after one or more amplification cycles or a reduced amount of condensation as compared to a control tube which has been subjected to the same cycles of amplification without a side-wall heater (50% less condensation, 80%, less condensation, 90% less condensation, 95% less condensation, 98% less condensation, 100% less condensation compared to a control tube) such that sample volume remains essentially the same throughout the reaction (at least 95%, 97%, 98%, and up to 100% of the sample volume does not change throughout the amplification reaction). Preferably, no condensation is observed after at least at least 10, at least 20, at least 25, at least 30, at least 35 cycles, at least 40 cycles, at least 45 cycles, or at least 50 cycles of amplification.

As used herein, the term "cycle" refers a series of temperature steps over selected time periods which result in the amplification of a target nucleic acid. A cycle minimally comprises a denaturing step and a primer annealing and extension step. In one aspect, a cycle comprises a denaturing step of 90-100° C. (preferably, 94° C.) for 30 seconds-1 minute (preferably, 30 seconds), an annealing step from 37° C.-60° C. (preferably, 55-57° C.) for 1-2 minutes (preferably 1 minute), followed by an extension step of 70-75° C. for 30 seconds to 2 minutes (preferably, for 30 seconds).

As used herein, an "amplification reaction" or a "PCR reaction" refers to a plurality of cycles which results in a desired amount of amplification or which is selected for a desired amount of amplification. In one aspect, a PCR reaction comprises at least 10, at least 20, at least 30, at least 40 or at least 50 cycles.

As used herein, "real time target template synthesis" or "real time synthesis" refers to a synthetic process (e.g., such as an amplification reaction) during which the synthesized product (e.g., double stranded DNA) can be analyzed as it is being generated without affecting subsequent synthesis of the product.

As used herein, a "sample" or a "test sample" refers to any substance comprising a target nucleic acid of interest. For example, a sample can comprise a cell, tissue or portion thereof, bodily fluid (including, but not limited to: blood; plasma; serum; spinal fluid; lymph fluid; synovial fluid; urine; tears; stool; external secretions of the skin, respiratory, intestinal and genitourinary tracts; saliva, and the like), organ or portion thereof; organism (e.g., bacteria) or portion thereof. A sample also can also be obtained from a natural source (e.g., such as a lake) or industrial source (e.g., such as a food product) suspected of comprising a biological material.

As used herein, a height of a side-wall heating block which is "substantially the same" as the longitudinal length of the upper portion of the sample tube refers to a height which varies by less than 5 mm from the longitudinal length of the upper portion of the sample tube, and preferably varies by less than 2 mm from the longitudinal length of the upper portion of the sample tube.

As used herein, a device "connectable" to another device refers to a device which is capable of forming an indirect or direct connection with the other device such that the output of at least one of the devices can be provided to the other device. For example, a heating element connectable to a power supply can at least receive power from the power supply to be activated by the power supply. In one aspect, output can be provided to the heating element through a direct electrical connection. A processor connectable to a power supply can, upon connection, transmit instructions to the power supply to direct the supply of power (e.g., in the form of a current) from the power supply to another device to which the power supply is connected (e.g., such as the heating element of the side wall heater). A processor connectable to a temperature sensor can receive temperature information from the temperature sensor upon connection and based on this information can transmit instructions to the power supply to activate or inactivate the heating element.

As used herein, maintaining a temperature for a "selected period of time" refers to a period of time identified by a user of the apparatus or by a program which is programmed into a processor connected to the apparatus. In one aspect, a selected period of time is the length of a PCR reaction (e.g., 20-50 cycles).

As used herein, a sample hole of said side-wall "conformed to receive" a particular size or shape of sample tube refers to a sample hole whose dimensions are substantially similar to the size and shape of a sample tube such that the sample tube snugly fits within the sample tube such that the sample tube does not freely rotate (i.e., without being manually or otherwise moved) within the sample hole or that there is less than 2 mm, and preferably less than 1 mm of space between the external wall of the sample tube and the walls of the sample hole.

As used herein, "at least one change of temperature" refers to a change of temperature which results in an at least 5° C., at least 11° C., at least 20° C., at least 40° C., or at least 50° C. change.

As used herein "maintaining a temperature for a selected period" refers to obtaining a temperature which remains substantially constant or "uniform" (e.g., does not vary by more than 3° C., preferably does not vary by more than 2° C., by more than 1° C., or by 0.5° C.).

Side-Wall Heater

The invention provides a side-wall heater for heating at least a portion of the side-walls of a sample tube, such as a PCR or eppendorf tube. Preferably, the heater is disposed in proximity to a sample block adapted for fitting into a thermocycling apparatus such that while the sample block provides cyclical changes of temperature to the lower portions of tubes disposed within sample wells of the sample block (e.g., as during a PCR reaction), the side-wall heater provides heat (either uniformly or in cycles) to the upper portion or the head space of the tubes.

Figure 8:
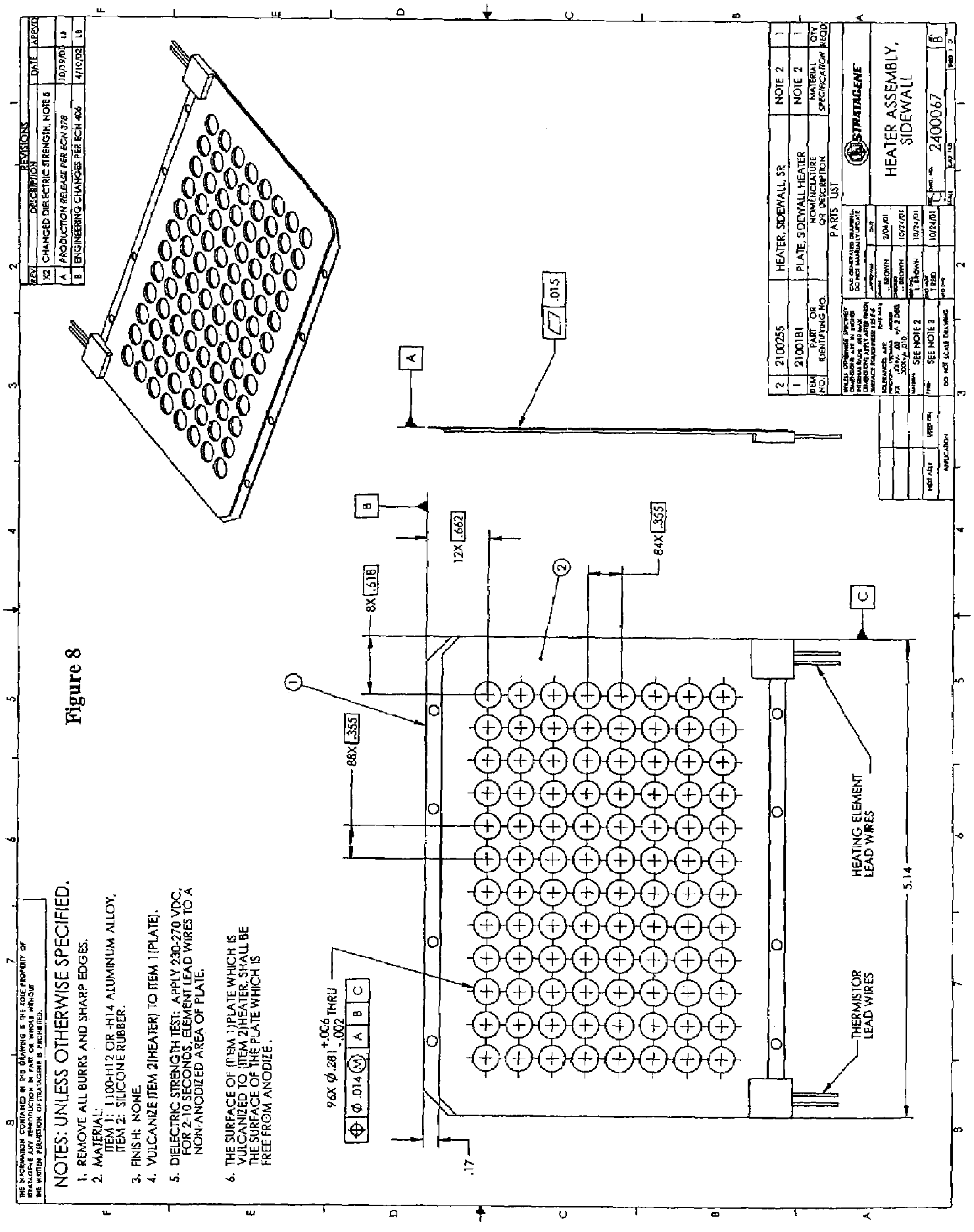
FIG. 8 is a diagram showing the specifications of the side-wall heater according to one aspect of the invention.

In one aspect, the side-wall heating apparatus is a heat conducting block (a "side-wall heating block"). In a preferred aspect, the side-wall heating block contains 96 sample holes in an 8 hole by 12 hole rectangular array on 9 millimeter centers and which comprises a heating element for heating the block (see, as shown in FIG. 2 and FIG. 8). In one aspect, the side-wall heating block is approximately the dimensions of an industry standard 96 well microtiter plate (see FIG. 8 for example). In another aspect, the side-wall heating block contains 384 sample holes and is approximately the dimensions of an industry standard 384 well microtiter plate. Other configurations also can be provided, e.g., 24 (3×8 sample holes), 32 (4×8 sample holes) or 48 sample holes (6×8 sample holes). It should be evident to those of skill in the art that the exact dimensions and numbers of sample holes of the heating block are not limiting and that varying dimensions and numbers of sample holes are encompassed within the scope of the invention.

The heating element preferably is a resistive heating element. In one aspect, a resistive heating element is used which is a thin metal film is applied to the side-wall heating block by using well-known methods such as sputtering, controlled vapor deposition and the like. The heating element also can be provided as a molded or machined insert (e.g., such as a cartridge) for incorporation into the side-wall heating block (e.g., into a hole machined into the heating block). Examples of heating elements include, but are not limited to those described in WO 94/05414, laminated thin film NiCr/polyimide/copper heaters, as well as graphite heaters. Peltier heaters also can be used. It should be obvious to those of skill in the art that many types of heaters are available or designable for heating heat conducting blocks and these are encompassed within the scope of the invention. In a preferred aspect, the heating element provides relatively uniform heating across the block (e.g., less than a 2° C., and preferably less than a 1° C. or 0.5° C. difference in temperature across the block).

The heating element preferably is electrically connected to a controllable power source for applying a current across the element. Control of the power source can be carried out by an appropriately programmed processor device (e.g., such as a computer) which receives signals from a temperature sensor in communication with the side-wall heating block. A wide variety of microsensors are available for determining temperatures, including, e.g., thermocouples having a bimetallic junction which produces a temperature dependent electromotive force (EMF), resistance thermometers which include material having an electrical resistance proportional to the temperature of the material, thermistors, IC temperature sensors, quartz thermometers and the like. See, e.g., Horowitz and Hill, *The Art of Electronics*, Cambridge University Press 1994 (2nd Ed. 1994).

In particular, the temperature measured by the temperature sensor and the input for the power source can be interfaced with a processor which is programmed to receive and record this data, e.g., via an analog-digital/digital-analog (AD/DA) converter. The same processor will typically include programming for directing the delivery of appropriate current from the power source to the heating element of the side-wall heating block for raising and lowering the temperature of block.

The sample holes of the side-wall heating block run from the top to the bottom of the block and are of sufficient depth and diameter such that the upper portion of a PCR tube can snugly fit within a sample hole. In one aspect, the side-wall heating block is from 0.5 mm to 5 mm deep, and preferably is on the order of 2 or 3 mm deep. In another aspect, the diameter of the sample holes of the side-wall heating block are sized to snugly fit the upper portion of a 0.2, 0.5, 0.6, or a 1.5 ml sample tube such as a PCR tube or eppendorf tube. As used herein, "snugly fit" means that a sample tube will not rotate within a given sample hole or that there is less than 2 mm, and preferably less than 1 mm of free space between the upper portion of the sample tube and the sample hole. A snug fit promotes the uniformity of thermal conductance across from the walls of the sample hole to the sample tube. However, in another aspect of the invention, the tubes loosely fit within the wells. Sample holes can be uniformly sized (e.g., all adapted to fit tubes of a given size) or non-uniformly sized (e.g., at least one sample hole is a different size from another sample hole).

Figure 1:
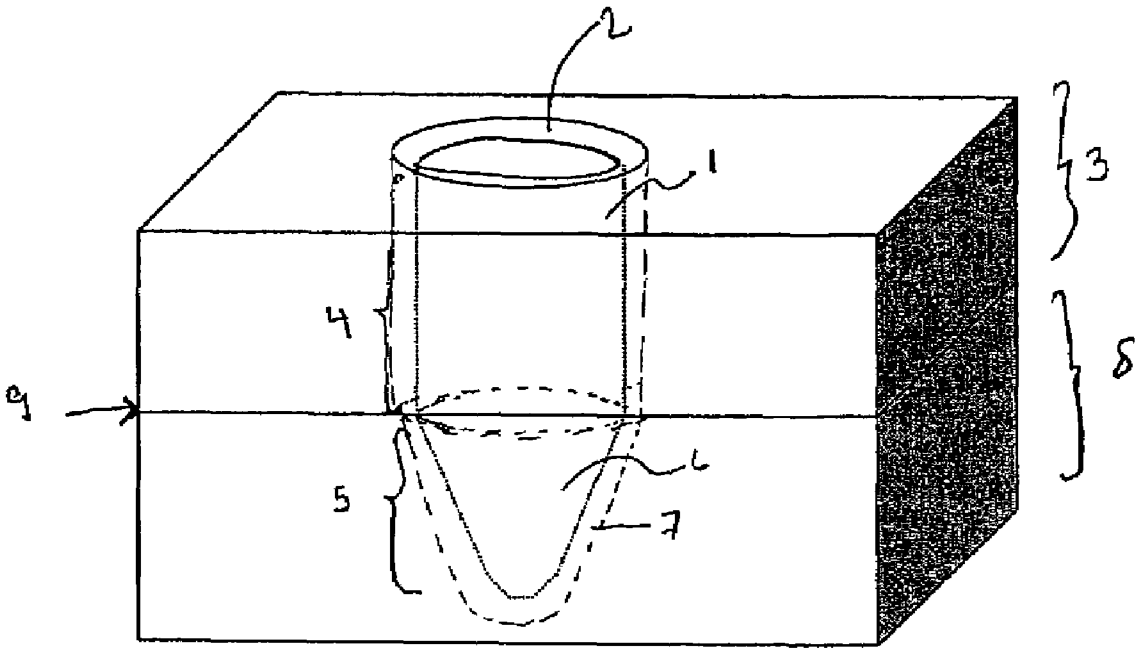
FIG. 1 is a schematic diagram of perspective view of an assembly comprising a side-wall heating block and a sample block for use in a thermocycler according to one aspect of the invention.

The side-wall heating block is designed so that when it is aligned with the sample block of a standard thermocycler, the holes in the side-wall heating block will align with the sample wells of the sample block which are adapted for receiving the lower portion of a sample tube, such a PCR tube or an eppendorf tube. In one aspect, the portion of the sample tube which snugly fits into a sample hole of the side-wall heating block is cylindrical while the portion of the sample tube which fits into the sample block is conical and therefore, the inner diameter of the sample holes in the side-wall heating block is generally constant while the inner diameter of the sample wells in the sample block may vary across the depth of the block. In one aspect, the lid of the sample tube will be level or slightly (less than 2 mm) above the upper surface of the side-wall heating block (see, as shown in FIG. 1); however, in another aspect, the lid of the sample will be raised above the upper surface of the block. For example when the sample tube is provided as part of a strip of sample tubes (see, as shown in FIG. 3), the "top" of the sample tube with respect to the side-wall heating block will extend from the portion of the tube which is level with or slightly above the upper surface of the side-wall heating block (see, arrow in FIG. 3).

In a preferred aspect, the invention provides an assembly comprising a side-wall heating block and a sample block in which the holes of the side-wall heating block and the sample wells of the sample block are aligned (see, e.g., as shown in FIG. 1). As shown in FIG. 1A, a tube 1 placed within a sample hole 2 of the side-wall heating block 3 will rest with its upper-portion or head space 4 in heat-conducting distance of the walls of the sample hole 2 (e.g., within 2 mm, and preferably within less than 1 mm of the walls, and can contact the walls of the sample hole, either directly or through a layer of heat conducting fluid such as mineral oil). However, in a preferred embodiment, there is no physical contact between the wall of the sample hole with the sidewall heater. The lower portion 5 of the tube 1 or the portion of the tube comprising a fluid 6 (e.g., such as a PCR reaction mixture) will rest in the sample wells 7 of the sample block 8. In a preferred aspect, the side-wall heating block and sample block are bonded together at their interface 9 (e.g., laminated together).

Preferably, the sample block is a heat-conducting block such as is typically found in a thermocycler. Still more preferably, the sample block is equipped with heating and cooling elements to enable the block, and therefore reaction mixture in the lower portion of sample tubes placed within the block, to cycle between different temperatures. Such elements are known in the art and are described in, for example, U.S. Pat. Nos. 5,602,756 and 6,197,595, the entireties of which are incorporated by reference herein.

In one aspect, the sample block provides a generally uniform temperature throughout the block (e.g., a temperature variance of less than 2° C., and preferably, less than 1° C. or 0.5° C. across the block) such that reaction mixtures in different sample tubes placed in the block experience the same PCR cycle even though they are spatially separated. In one aspect, the sample block is adapted for use in a thermocycler such as Stratagene®'s Mx 4000 or RoboCycler® thermocycler.

Figure 7:
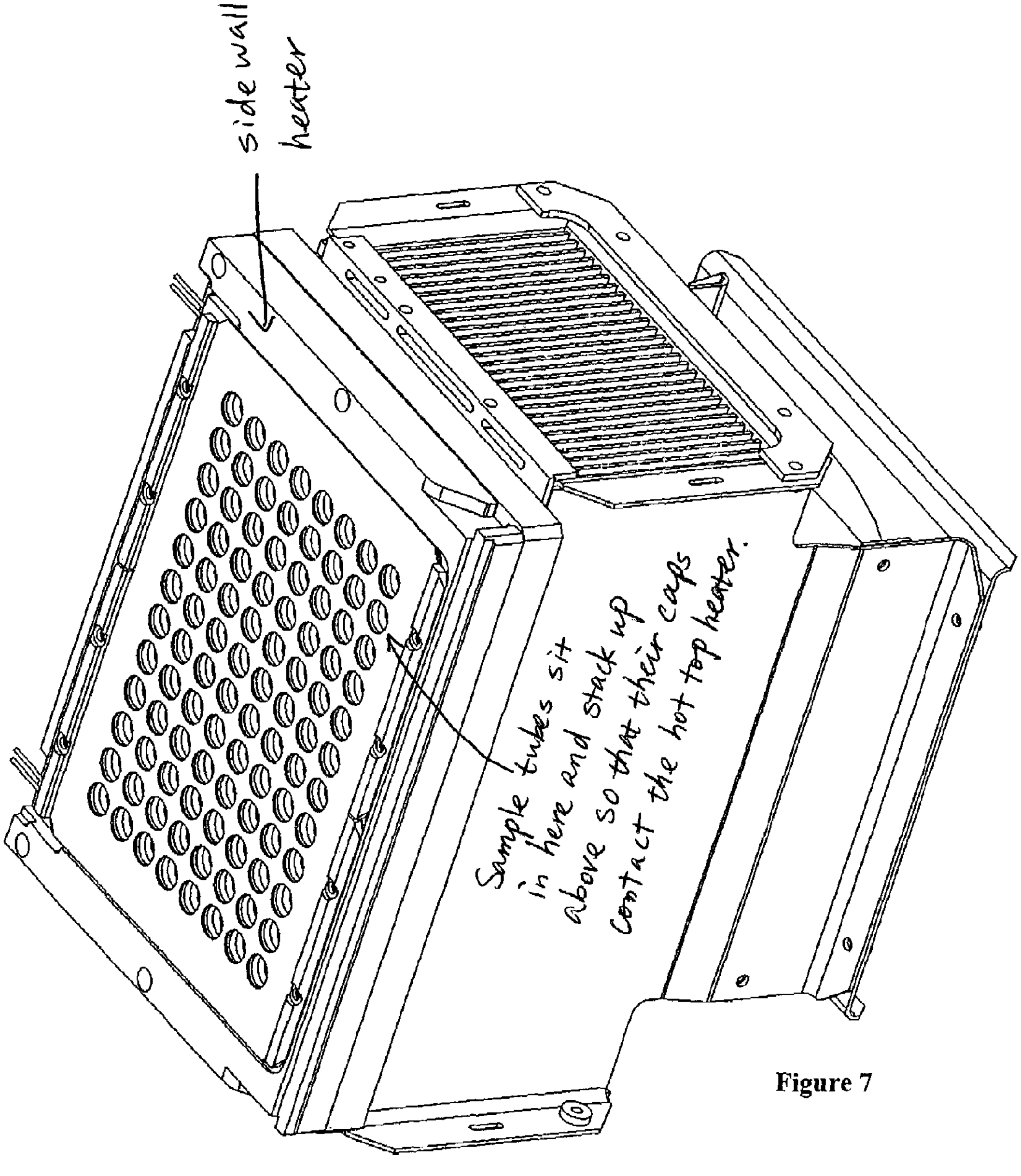
FIG. 7 is a figure illustrating the assembly of the side-wall heater according to one aspect of the invention.

The side-wall heating block can be removably attached to the sample block; however, in one aspect, as discussed above, the side-wall heating block is integrally attached to the sample block, e.g., such as by laminating the heating block to the sample block (see FIG. 7 for example). However, preferably, the heating element of the side-wall block is controlled independently of the heating element of the sample block. In one aspect, while the sample block cycles through at least two temperature ranges differing by at least 10° C., at least 15°, at least 20° C., at least 30° C., at least 40° C., or at least 50° C., or at least 55° C., the side-wall heating block remains at a substantially constant temperature over time (e.g., the temperature of the side-wall heating block does not vary more than 2° C., preferably, no more than 1° C., and still more preferably, no more than 0.5° C., over at least 10 to 50 PCR cycles). The sample block can be equipped with a block temperature servo feedback loop which has a time constant for reacting to stimuli so that the temperature of the sample block is not changed at a rate faster than a control system in communication with the sample block can respond to temperature errors (e.g., such as the processor system of a thermocycler device).

The side-wall heating block preferably heats at least a portion of the sample tube (preferably the upper portion or head space portion) to a temperature above the evaporation and condensation point of water or a reaction mixture such as is used in amplification reactions, such that no evaporation and condensation and refluxing occurs within the sample tube. This reduces or minimizes temperature variations from sample to sample during an amplification reaction which occurs during the thermocyling process. In a preferred aspect, the side-wall heating block maintains a temperature, which is at least the same as, but which is preferably at least 0.5-10° C. higher than the temperature of the temperature achieved during the denaturing phase of a PCR reaction. For example, the side-wall heating block preferably maintains a temperature greater than 89° C., greater than 94° C., or greater than 99° C. The temperature rise is limited to some maximum safe level by the inherent rise in resistance of the heating element.

In one aspect, the temperature of the side-wall heating block is the same as the temperature of an external heater in proximity to the top of the sample tubes. As used herein, "proximity" refers to a close enough distance in which heat can be conducted to the tops of the tubes from the assembly without substantial dissipation (e.g., less than 5° C. loss of heat, preferably, less than 2° C., or less than 1° C. or 0.5° C.). For example, in one aspect, the temperature of the side-wall heating block can be set to the same temperature as a hot top being used with a standard PCR device.

In another aspect, the temperature of the side-wall heating block is varied. This may be preferable, for example, when the side-wall heating block is used in conjunction with a Hot Top Assembly™ hot top such as provided by Stratagene® for the Robocycler® thermocycler. Unlike other hot tops, the Hot Top Assembly™ hot top can be used to vary the temperature provided at the tops of sample tubes. Therefore, in one aspect, the temperature of the side-wall heating block is cycled along with the temperature of the Hot Top Assembly™ hot top. For example, when an extension cycle (e.g., such as a 55° C. cycle) is occurring in the sample block, the Hot Top Assembly™ hot top may be cycling through an 85° C. cycle. A temperature sensor within the Hot Top Assembly™ hot top will communicate this information to a processor in communication with the side-wall heating block and the processor will provide an amount of current to the resistive heating element (via the power source) appropriate to heat the side-wall heater to 85° C. The temperature of the side-wall heating block itself is regulated by feedback between a temperature sensor in communication with the side-wall heating block and the processor. When a denaturing cycle is occurring in the sample block, the temperature of the Hot Top Assembly™ hot top may be increased to a temperature about the same or higher than the temperature of the denaturing cycle (e.g., to about 96-100° C.) and the side-wall heating block also can be heated to the same temperature (e.g., about 96-100° C.). Preferably, the temperature of the side-wall heater is regulated independently of the temperature of both the Hot Top Assembly™ hot top and the sample block. The processor in communication with the side-wall heater and the Hot Top Assembly™ hot top may be programmed to take the side-wall heater and assembly, independently through any number of predetermined time/temperature profiles. Cooling of the side-wall heating block can occur through exposure to ambient temperature given the thinness of the block; however, additional cooling elements may be included if desired, e.g., coolant systems, Peltier coolers, water baths, etc, as are known in the art.

The side-wall heating block can be machined out of a solid block of a heat conducting metal such as aluminum alloy. The walls of sample holes are drilled to match the orientation and position of sample wells in a sample block for a PCR thermocycler as described above. Generally, the same materials used for the sample block can be used for the side-wall heating block.

In some aspects, it may be desirable to independently control the amount of heat delivered to individual sample tubes at different sample holes. Therefore in one aspect, the side-wall heating block comprises a plurality of individual cylindrical heating elements disposed within the wells of the sample holes. For example, cylindrical heating elements comprising a conductive ring made of polymeric materials with resistive function can be used. Resistive conductors preferably comprise a suitable conductive composite material such as carbon black, graphite, silver, etc., and a polymeric binder such as polyethylene, polyamides, thermoplastic polyesters, acetal resins, PEEK, PES, PPS, and the like, and may contain non-electrically-conductive fillers such as plasticizers, inert fillers, lubricants, stabilizers, and the like. However, in another aspect, the cylindrical element can comprise an electrically insulating material (e.g., ceramic or mica) which itself comprises one or more spirals or windings of alloys (e.g., such as NiCr) which can be used to provide resistive conductors. Independent electrical connections between the cylindrical heating elements and power supply/processor can be used to provide variation in the amount of heat delivered to sample holes in the side-wall heating block. In this aspect, it is preferable that the side-wall heating block not be made of a heat conducting material so that the delivery of heat to individual sample tubes can be controlled through the cylindrical heating elements.

In still another aspect, asymmetrically locating heat resistive element(s) within the side-wall heating block can be used to create a temperature gradient across the side-wall heating block. For example, a heat resistive cartridge can be place at one edge of the block but not at another, resulting in a temperature gradient which extends from the edge of the block to the other.

Methods of Increasing Amplification Uniformity Using Side-Wall Heaters

In one aspect, the invention provides a method for increasing the uniformity of a thermocycling reaction by reducing or preventing evaporation and condensation during the thermocycling reaction. The method comprises providing a sample tube comprising a reaction mix (e.g., nucleotides, primers, polymerase, a suitable buffer, and a sample containing or suspected of containing target nucleic acids, where the reaction is PCR) and placing the sample tube within an assembly comprising a side-wall heating block according to the invention and a sample block such that the upper portion or head space of the tube is within heat-conducting distance of the wall of the sample holes in the heating block and the remaining lower portion of the tube (e.g., comprising the reaction mixture) is within heat-conducting distance of the walls of the sample wells of the sample block. Preferably, "heat-conducting distance" is less than 2 mm. More preferable, heat conducting distance is less than 1 mm.

The heating element in the side-wall heating block is activated by a power supply in electrical communication with the heating element in response to programmed instructions from a processor in communication with both the power supply and a temperature sensor in the side-wall heating block. In response to this activation, the block is heated to a selected temperature and transfers heat to the upper portions of one or more tubes placed in the sample holes of the block. Preferably, this selected temperature is a temperature above the temperature of the reaction mixture in the lower portion of the sample tube.

In a preferred aspect, the sample block beneath the side-wall heating block provides cycles of heating and cooling, thereby cycling the reaction mix in the lower portion of the tube through different temperature steps. In this aspect, the side-wall heating block is preferably at a temperature which is the same or higher than the highest temperature reached by the sample block. For example, if the sample block reaches a high temperature of 94° C. during one of its cycles (e.g., such as during the denaturing step of a PCR reaction), the side-wall heating block is heated to 94° C. or higher. Preferably, the side-wall heating block maintains a temperature which is always higher than the temperature of the reaction mix in the tube, and consequently the upper portion or head space of the tube will always be at a temperature which is the same or higher than the temperature of the reaction mix in the lower portion of the tube. As a consequence, condensation of sample onto the side-walls of the tube is reduced or eliminated. This provides increased uniformity during an amplification reaction as well as decreased sample loss.

It should be obvious that any amplification scheme which relies on thermal cycling can be performed using the apparatus and assembly according to the invention. Exemplary amplification schemes that may be employed with the invention include PCR, ligase-based amplification schemes, such as ligase chain reaction (LCR), Q-beta replicase-based amplification schemes, strand displacement amplification (SDA) schemes, such as described by Walker et al, Nucleic Acids Research, 20:1691-1696 (1992), and the like. A comprehensive description of nucleic acid amplification schemes is provided by Keller and Manak, *DNA Probes*, Second Edition (Stockton Press, New York, 1993).

Preferably, the assembly comprising the side-wall heating block and the sample block is placed in or has been previously disposed in a thermocyler. The thermocycler comprises minimally a receiving area for the sample block and can be of a conventional design such as is known in the art. Preferably, the thermocycler comprises a lid adapted to connect with input and output elements (e.g., a light source and light transmitting element, respectively) of a detection system for monitoring the synthesis of nucleic acids in reaction mixtures within sample tubes in the assembly in real time. In this aspect, the sample tubes are preferably capped with transparent lids through which optical signals can pass to detector.

In one aspect, an optically detectable label is used for monitoring the formation of amplification products (e.g., copies of target nucleic acids). For example, a fluorescent labeled molecule can be integrated into newly synthesized nucleic acid molecules (e.g., by providing fluorescently labeled nucleotides which can be incorporated into amplified molecules during primer extension reactions or by providing fluorescently labeled primers). The fluorescently labeled molecule is capable of emitting a detectable signal when appropriately excited (e.g., during at least the extension portion of each cycle of a PCR reaction). The amplification reaction is performed for a sufficient time (e.g., for an appropriate number of cycles) to establish a desired final concentration of an amplified nucleic acid product.

The detection system preferably consists of a light source (e.g., a visible light laser or an ultraviolet lamp), fiber optic connectors and light tubes connected between the top of the sample tubes in the side-wall heater/sample block assembly, and one or more scanning optical fibers for transmitting light to and receiving light from sample tubes within the assembly. Preferably, a plurality of optical fibers (e.g., one per different type of optical signal or label being detected) is used to scan the surface of the tubes (e.g., row by row) collecting a plurality of optical signals per scan (preferably at least 9 optical signals) which are averaged to generate an average signal per sample tube per scan. Preferably, the detector also comprises suitable signal amplification and conversion circuitry for converting light signals to a digital input to the processor which is in communication with the assembly. The detector also may comprise a digital camera system such as described in the Higuchi et al., 1993, *Biotechnology* 11(9): 1026-30.

The output of the detection system (e.g., signals corresponding to those generated during the amplification reaction) is fed to the processor for data storage and manipulation. In one embodiment, the system detects multiple different types of optical signals, such as multiple different types of fluorescent labels and has the capabilities of a microplate fluorescence reader (e.g., is able to isolate and analyze the intensity of signals obtained from individual wells).

The detection system is preferably a multiplexed fluorimeter containing an excitation light source, which may be a visible light laser or an ultraviolet lamp, a multiplexer device for distributing the excitation light to the individual reaction tubes through the fiber optic tubes and connectors for receiving fluorescent light from the reaction tubes, a filtering means for separating the fluorescence light from the excitation light by their wavelengths, and a detection means for measuring the fluorescence light intensity.

Preferably, the detection system of the thermocycler provides a detection range of 350 nm to 830 nm, allowing greater flexibility of fluorophore choice, providing high sensitivity and excellent signal-to-noise ratio. The system's light source preferably generates an extended excitation range from 350 to 750 nm. This enables a user to choose fluorophores with little or no spectral overlap, producing clean, delineated signals for superior multiplexing. Optimized interference filters also can be provided to precisely match the excitation and emission wavelengths of each fluorophore whose intensity is being evaluated, to block out unwanted cross-talk from spectrally adjacent fluorophores. For example, FAM, TET, HEX/JOEVIC, TAMRA, Texas Red/ROX, Cy5 and Cy3 filter sets are available commercially and custom filter sets can be made for other fluorophores (Stratagene, Calif.).

Preferably, real-time amplification plots are viewed as amplification progresses. This enables a user of the assembly to determine at a glance how an experiment is running at any time during thermal cycling, rather than waiting until the end of the run. A user can choose to abort a run if a problem develops in a reaction, or stop the experiment and save the data as soon as the desired information is generated.

Optical signals received by the detection system (e.g., corresponding to fluorescent signal intensity at a given time point in a given tube) are generally converted into signals which can be operated on by the processor to provide data which can be viewed by a user on a display of a user device (e.g., a computer) in communication with the processor. Examples of data which can be displayed include amplification plots, scatter plots, sample value screens for all the tubes in the assembly and for all labels used, an optical signal intensity screen (e.g., fluorescent signal intensity screen), final call results, melting curves, annealing ranges, text reports, and the like. The user device also can display a user interface to enable a user to provide instructions to the processor; for example, instructions to change the temperature of the side-wall heater and/or the sample block and/or a hot top, if this is also part of the thermocycler system.

FIG. 4 shows a table of data obtained during real-time PCR performed using the assembly according to the invention in a Stratagene® Mx4000 thermocycler (condition: 30 seconds at 95° C., 60 seconds at 55° C., 30 seconds at 72° C.). As can be seen from the table, there is enhanced uniformity in the amplification of target nucleic acids using the assembly. This is shown graphically in FIGS. 2B and 2C for reactions occurring in sample tubes arrayed in 8 columns and 12 rows in the side-wall heating block. As can be seen from the Figures, the well-well variation in signal intensity during the amplification reaction is minimal.

Variations, modifications, and other implementations of what is described herein will occur to those of ordinary skill in the art without departing from the spirit and scope of the invention as described and claimed herein.

All of the references, including patents and patent applications, identified above are hereby expressly incorporated herein by reference in their entireties.

What is claimed is:

1. A thermocycling apparatus comprising:

(a) a sample block having a top surface and at least one sample well for receiving a sample tube, said sample block having the ability to cycle between different temperatures;

(b) a sample tube having an upper portion and a lower portion, said upper portion being the portion protruding past the top surface of said sample block;

(c) a side-wall heating block comprising a heat-conducting material, said heat-conducting material comprising at least one sample hole for receiving at least a part of the upper portion of the sample tube; wherein said sample hole runs from an upper surface of said side-wall heating block through a lower surface of said side-wall heating block, said sample hole alignable with said sample well, wherein said side-wall heating block is selected to heat only the upper portion of the sample tube, and wherein said lower portion of said sample tube protrudes past the lower surface of said side-wall heating block;

(d) a heating element disposed on or in said side-wall heating block, said heating element connectable to a power supply for activating said heating element to thereby provide heat to the heat-conducting material; and (e) a processor programmed to cycle the temperature of said sample block said processor also programmed to maintain the temperature of said side-wall heating block at a temperature that is greater than the temperature of said sample block while said sample block is cycled.

2. The apparatus according to claim 1, wherein the side-wall heating block further comprises:

(a) a temperature sensor for detecting the temperature of the side-wall heating block, said temperature sensor connectable to said processor for monitoring the temperature of the side-wall heating block, said processor connectable to said power supply and for providing instructions to said power supply to activate said heating element to maintain the temperature of the side-wall heating block to a level which is higher than the temperature of a fluid in said lower portion of said tube.

3. The apparatus according to claim 1, wherein said side-wall heating block comprises a plurality of sample holes for receiving a plurality of sample tubes.

4. The apparatus according to claim 1, wherein at least one sample hole is conformed to fit a sample tube for use in a PCR reaction.

5. The apparatus according to claim 4, wherein said sample tube can receive up to 0.2 ml of a fluid.

6. The apparatus according to claim 4, wherein said sample tube can receive up to 0.6 ml of a fluid.

7. The apparatus according to claim 4, wherein said sample tube can receive up to 1.5 ml of a fluid.

8. The apparatus according to claim 4, wherein said sample tube is connected to a plurality of other sample tubes, each other sample tube received by a sample hole in the side-wall heating block, and wherein the top of each tube extends from the portion of the tube which rests at the top of the sample hole.

9. The apparatus according to claim 4, wherein said sample tube can receive up to 0.5 ml of a fluid.

10. The apparatus according to claim 1, wherein said side-wall heating block and said sample block comprise 24 sample holes.

11. The apparatus according to claim 1, wherein said side-wall heating block and said sample block comprise 32 sample holes.

12. The apparatus according to claim 1, wherein said side-wall heating block and said sample block comprise 48 sample holes.

13. The apparatus according to claim 1, wherein said side-wall heating block and said sample block comprise 96 sample holes.

14. The apparatus according to claim 1, wherein said side-wall heating block and said sample block comprise 384 sample holes.

15. The apparatus according to claim 14, wherein said sample holes are arrayed in three, four, six, or twelve columns.

16. The apparatus according to claim 1, wherein said sample holes are arrayed in 8 rows.

17. The apparatus according to claim 1, wherein said heating element is a resistive heating element.

18. The apparatus according to claim 1, wherein said sample block for said thermocycler comprises a heating element in said sample block and said heating element in said side-wall heating block is controllable independently of said heating element in said sample block.

19. The apparatus according to claim 1, wherein said sample block further comprises a cooling element.

20. The apparatus according to claim 1, wherein said at least one sample well in said sample block is beveled to receive a conical portion of a sample tube.

21. The apparatus according to claim 20, wherein said sample hole of said side-wall heating block is conformed to receive a cyclindrical portion of a sample tube comprising a cyclindrical upper portion and a conical lower portion.

22. The thermocycler apparatus according to claim 1, wherein said device further comprises a hot top for heating the external surface of the top of said at least one sample tube placed in a sample hole in said side-wall heating block.

23. The thermocycler apparatus according to claim 1, wherein said device is connectable to a detector for detecting optical signals from said at least one sample tube disposed in said assembly.

24. The thermocycler apparatus according to claim 23, wherein said detector enables detection of a signal generated during an amplification reaction.

25. A method for heating the upper portion of a sample tube above a portion of the tube which is filled with a fluid, said method comprising:

a) placing said sample tube in a sample hole of an apparatus for heating an upper portion of the interior of a sample tube, said upper portion extending from the top of the tube to a point above a lower portion of the tube which is filled with a fluid, wherein said apparatus comprising:

(i) a side-wall heating block comprising a heat-conducting material, said heat-conducting material comprising at least one sample hole for receiving the sample tube; wherein said sample hole runs from an upper surface of the block through a lower surface of said block, said sample hole alignable with a sample well of a sample block for a thermocycler apparatus, wherein the height of said side-wall heating block is substantially the same as the longitudinal length of the upper portion of the sample tube; and (ii) a heating element disposed on or in said side-wall heating block, said heating element connectable to a power supply for activating said heating element to thereby provide heat to the heat-conducting material, wherein said portion of said tube comprising said fluid protruding past said lower surface of said side-wall heating block; and b) activating said heating element, to heat said upper portion of said sample tube.

26. The method according to claim 25, wherein said side-wall heating block is heated to a temperature which is the same or above the temperature of said portion of said tube comprising said fluid.

27. The method according to claim 25, wherein heating of said side-wall heating block prevents condensation on interior walls of said sample tube.

28. The method according to claim 25, wherein said portion of said tube comprising said fluid is within a sample well of a sample block, said sample block comprising a heating element which controlled independently of said heating element in said side-wall heating block.

29. The method according to claim 28, wherein said sample block cycles said portion of said tube comprising said fluid through a least one change of temperature.

30. The method according to claim 29, wherein said sample block cycles said portion of said tube comprising said fluid through cycles of a PCR reaction.

31. The method according to claim 30, wherein said heating element maintains said side-wall heating block at a temperature which is above the highest temperature through which the sample block is cycling.

32. The method according to claim 31, wherein said highest temperature is greater than 90° C.

33. The method according to claim 31, wherein said highest temperature is 94° C.

34. The method according to claim 28 or 29, wherein heating element maintains said side-wall heating block at a temperature which is the same or above the temperature of the sample block for a selected period of time.

35. The method according to claim 34, wherein said side-wall heating block maintains a uniform temperature while said sample block is cycling through changes of temperature.

36. A thermocycling apparatus comprising:

(a) a sample block having a top surface and at least one sample well for receiving a sample tube, said sample block having the ability to cycle between different temperatures;

(b) a sample tube having an upper portion and a lower portion, said upper portion being the portion protruding past the top surface of said sample block;

(c) a side-wall heating block comprising a heat-conducting material, said heat-conducting material comprising at least one sample hole for receiving at least a part of the upper portion of the sample tube, wherein said sample hole runs from an upper surface of said side-wall heating block through a lower surface of said side-wall heating block, said sample hole alignable with said sample well, wherein said side-wall heating block is selected to heat only the upper portion of the sample tube, and wherein said lower portion of said sample tube protrudes past the lower surface of said side-wall heating block;

(d) a heating element disposed on or in said side-wall heating block, said heating element connectable to a power supply for activating said heating element to thereby provide heat to the heat-conducting material; and (e) a hot top for heating the external surface of the top of said at least one sample tube placed in a sample hole in said side-wall heating block.

37. The apparatus according to claim 36, wherein the side-wall heating block further comprises:

(f) a temperature sensor for detecting the temperature of the side-wall eating block, said temperature sensor connectable to a processor for monitoring the temperature of the side-wall heating block, said processor connectable to said power supply and for providing instructions to said power supply to activate said heating element to maintain the temperature of the side-wall heating block to a level which is the same or higher than the temperature of a fluid in said lower portion of said tube.

38. The apparatus according to claim 36, wherein said sample block further comprises a cooling element.

39. The apparatus according to claim 36, wherein said device is connectable to a detector for detecting optical signals from said at least one sample tube disposed in said assembly.

40. The apparatus according to claim 39, wherein said detector enables detection of a signal generated during an amplification reaction.

* * * * *

UNITED STATES PATENT AND TRADEMARK OFFICE

CERTIFICATE OF CORRECTION

PATENT NO. : 7,459,302 B2
APPLICATION NO. : 10/261751
DATED : December 2, 2008
INVENTOR(S) : Reid et al.

It is certified that error appears in the above-identified patent and that said Letters Patent is hereby corrected as shown below:

In column 15, line 10, in Claim 21, delete “cyclindrical” and insert -- cylindrical --, therefor.

In column 15, line 11, in Claim 21, delete “cyclindrical” and insert -- cylindrical --, therefor.

Signed and Sealed this

Fourteenth Day of July, 2009

JOHN DOLL
*Acting Director of the United States Patent and Trademark Office*